(12) United States Patent
Brown, Jr.

(10) Patent No.: US 6,340,234 B1
(45) Date of Patent: Jan. 22, 2002

(54) ILLUMINATED LENS DEVICE FOR WELDERS HELMET

(76) Inventor: Manning Brown, Jr., 126 Coolidge Ave., Amityville, NY (US) 11701

( * ) Notice: Subject to any disclaimer, the term of this patent is extended or adjusted under 35 U.S.C. 154(b) by 0 days.

(21) Appl. No.: 09/628,769

(22) Filed: Jul. 31, 2000

(51) Int. Cl.$^7$ .............................................. F21V 21/084
(52) U.S. Cl. ...................................... 362/105; 362/106
(58) Field of Search ............................... 2/5, 15, 10, 9, 2/424, 422, 909, 918, 905, 906; 219/147; 362/103, 105, 106, 276, 800

(56) References Cited

U.S. PATENT DOCUMENTS 2,045,802 A * 6/1936 Richter ....................... 219/147
4,283,798 A * 8/1981 Kuehn ......................... 362/105
6,113,243 A * 9/2000 Saul ............................ 362/106

* cited by examiner

*Primary Examiner*—Y. My Quach-Lee
(74) *Attorney, Agent, or Firm*—Michael I. Kroll

(57) ABSTRACT

The present invention 10 discloses means to illuminate 34 the lens 24 of a face shield 36 to be worn by a welder 12. The lens 24 is illuminated to enable the welder 12 to see through the lens 24 prior to the welding arc 20 being lighted. The face shield 36 is equipped with a size adjustable head band 30. Multiple lights 34 are disposed around the frame 46 of the lens and an on/off switch 28 is provided along with a time delay button 26. The lights 34 are powered by a battery 42 which is disposed in frame 46. The present invention 10 can be retrofitted onto existing helmets or manufactured as an integral part of new helmets/face shields.

12 Claims, 10 Drawing Sheets

ILLUMINATED LENS DEVICE FOR WELDERS HELMET

BACKGROUND OF THE INVENTION

1. Field of the Invention

The present invention relates generally to welding equipment and, more specifically, to an illuminated lens device having a housing having a shaded lens therein having a plurality of spaced apart circumferentially positioned lights which can be selectively illuminated by a switch whereby the wearer of the illuminated lens device will be able to see through the normally dark lens.

Further, the illuminated lens device has a compartment for the placement therein of a power source, such as batteries. In addition, the electric circuit for the illuminated lens device has a timer switch incorporated therein, whereby the user can vary the duration of illumination.

The illuminated lens device of the present invention can be retrofitted to existing helmets or can be manufactured as an integral part of new helmets.

2. Description of the Prior Art

There are other lighting devices device designed for use with headgear. Typical of these is U.S. Pat. No. 4,332,004 issued to Slaughter on May 25, 1982.

Another patent was issued to Sabalvaro, Jr. on Sep. 16, 1997 as U.S. Pat. No. 5,667,292. Yet another U.S. Pat. No. 5,741,060 was issued to Johnson on Apr. 21, 1998 and still yet another was issued on Sept. 14, 1999 to Bradley as U.S. Pat. No. 5,951,141.

U.S. Pat. No. 4,332,004

Inventor: Grimes G. Slaughter

Issued: May 25, 1982

A lighting system for a welders helmet which includes a high intensity, high Kelvin temperature electric light source attached to the face shield for directing a high energy, high Kelvin temperature light beam forwardly of the viewing port, and an energizing circuit including an on-off switch interconnecting the light source to a source of electrical energy which deenergizes the light source where the welde's eyes are not protected by the face shield.

U.S. Pat. No. 5,667,292

Inventor: Valentin C. Sabalvaro, Jr.

Issued: Sept. 16, 1997

A portable light that is hands-free, out of the way, adjustable, and automatically directed to the user's line of sight by virtue of his head movement. This is accomplished by taking a topless hat, commonly known as the visor, and building around it to form a portable light that is worn on the head. Said visor would have battery casing molded at the base of the brim closest to the forehead to minimize the downward pull of the battery's weight. The bulb assembly housing unit is attached to the front of the brim by means to allow pivotal movement thus allowing for the light to he directed forward or downward, or at any angle in between.

U.S. Pat. No. 5,741,060

Inventor: Thomas R. Johnson

Issued: Apr. 21, 1998

A combination baseball style cap and light assembly, wherein the cap has a crown, a bill extending from the crown, a sweatband liner circumscribing the bottom edge of the cap, and a reinforcing crown liner, has a double light and switch assembly comprising two lamp sockets affixed to a mounting plate on each side of a sealed sub-mini micro switch also affixed to the mounting plate. The plate is in turn affixed to the underside of the bill of the cap, two lamp sockets affixed to the mounting plate such that their axes decline at an acute angle to the plane of the plate and converge at an acute angle to a line perpendicular to the front edge of the plate, setting the focal point of the lamps at a predetermined location directly out from and generally equidistant between the wearers eyes. A micro switch is affixed to an integral mounting flange on the mounting plate located approximately on the center line of the mounting plate between the two sockets. First and second battery holders are each affixed respectively to each side of the center line of the top edge of the reinforcing element of the crown of the cap and the top edge of the crown of the cap, and a circuit electrically couples the micro switch, the lamp sockets and the battery holders.

U.S. Pat. No. 5,951,141

Inventor: Paul David Bradley

Issued: Sept. 14, 1999

A head mounted illumination device including a light source disposed within a housing. The light source includes a plurality of lights disposed within the housing. The housing is securable to a mouthpiece of a headset to facilitate securement of the light source to the headset. An activation button is disposed within the housing. The activation button is in communication with the light source. The activation button includes a contact switch extending outwardly of the housing. The contact switch aligns with a lip of a user. A power source is securable to the headset. The power source includes wiring extending outwardly therefrom. The wiring couples with the activation button to facilitate communication therewith.

While these headgear lighting devices may be suitable for the purposes for which they were designed, they would not be as suitable for the purposes of the present invention, as hereinafter described.

SUMMARY OF THE PRESENT INVENTION

The present invention discloses means to illuminate the lens of a face shield to be worn by a welder. The lens is illuminated to enable the welder to see through the lens prior to the welding arc being lighted. The face shield is equipped with a size adjustable head band. Multiple lights are disposed around the frame of the lens and an on/off switch is provided along with a time delay button. The lights are powered by a battery which is disposed in frame. The present invention can be retrofitted onto existing helmets or manufactured as an integral part of new helmets/face shields.

A primary object of the present invention is to provide an illuminated lens device for selectively seeing through a normally dark lens.

Another object of the present invention is to provide light for the welder to see by before the arc powered. Also to provide a light which mounts to an attachment shield around the viewing lens.

Yet another object of the present invention is to provide light for the welder to see by before the arc powered. Also to provide a light which mounts to an attachment shield around the viewing lens. A light which is directed toward the lens so that the welder can see the work before the arc is started.

Still yet another object of the present invention is to provide light for the welder to see by before the arc powered. Also to provide a light which mounts to an attachment shield around the viewing lens. A light which is directed toward the lens so that the welder can see the work before the arc is started. Lens light is controlled by a button on the face shield, the light has a timer which will allow the welder to turn the lens light on and get into position and is powered by batteries.

Yet another object of the present invention is to provide light for the welder to see by before the arc powered. Also to provide a light which mounts to an attachment shield around the viewing lens. A light which is directed toward the lens so that the welder can see the work before the arc is started. Lens light is controlled by a button on the face shield, the light has a timer which will allow the welder to turn the lens light on and get into position, and is powered by batteries. After a predetermined length of time, the welder should have started the arc and can see by that light.

Additional objects of the present invention will appear as the description proceeds.

The present invention overcomes the shortcomings of the prior art by providing light for the welder to see by before the arc powered. Also to provide a light which mounts to an attachment shield around the viewing lens. A light which is directed toward the lens so that the welder can see the work before the arc is started. Lens light is controlled by a button on the face shield, the light has a timer which will allow the welder to turn the lens light on and get into position, and is powered by batteries. After a predetermined length of time, the welder should have started the arc and can see by that light.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawings in which.

LIST OF REFERENCE NUMERALS

Figure 1:
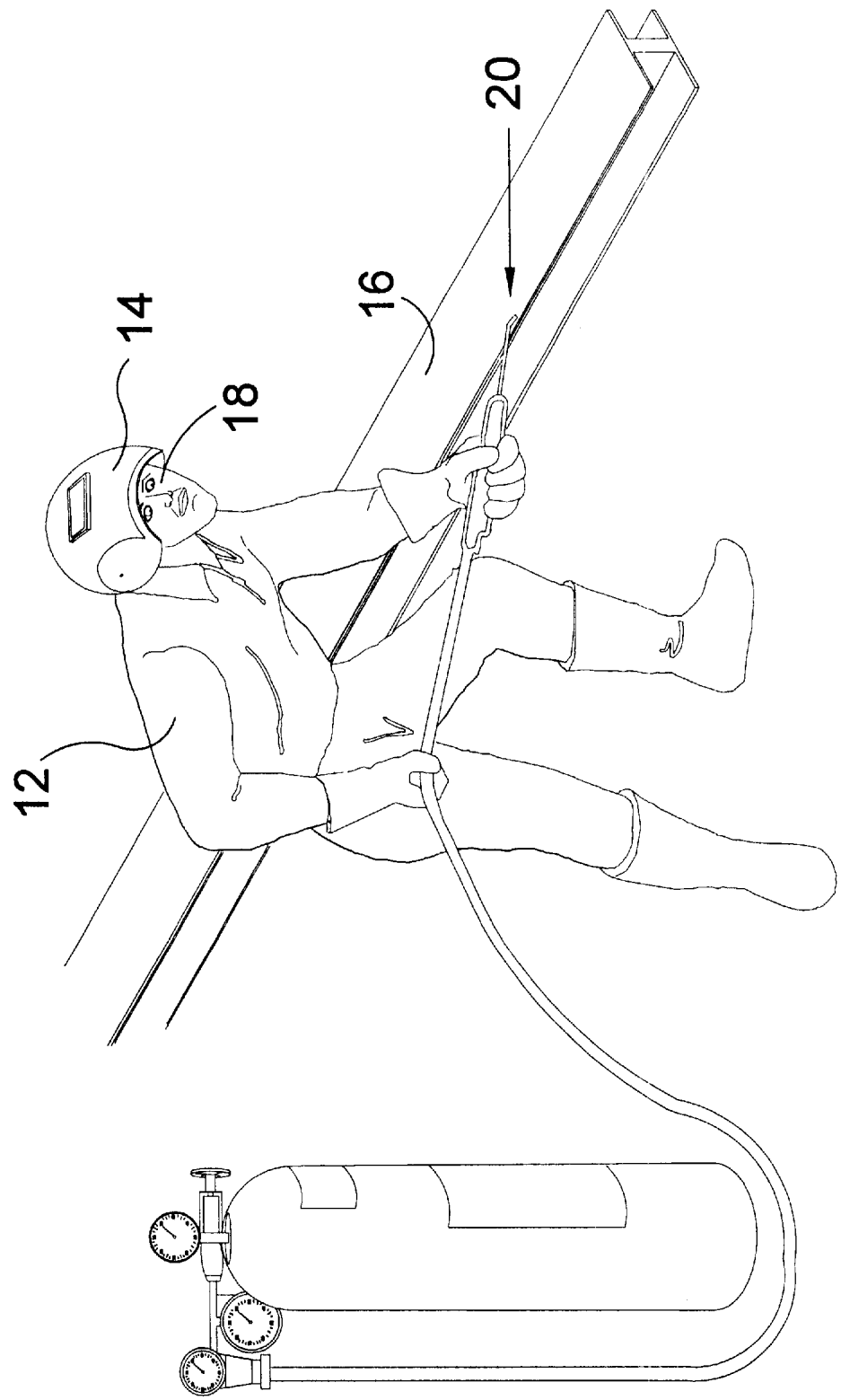
FIG. 1 is a perspective illustration depicting a welder wearing conventional arc welding safety, equipment. Welders are constrained by the equipment which is designed to provide them with a certain level of safety. The welder must jerk the protective face shield down while simultaneously trying to start the arc, keeping in mind the location of his work.

With regard to reference numerals used, the following numbering is used throughout the drawings.

10 present invention
12 welder
14 conventional face shield
16 workpiece
18 eyes
20 welding arc
22 flash
24 lens
26 delay timer
28 on/off switch 30 head band
32 head
34 lens lights
36 helmet
38 size adjustment means
40 battery doors
42 battery compartment
44 electrical connection means
46 frame

DESCRIPTION OF THE PREFERRED EMBODIMENT(S)

In order that the invention may be more fully understood, it will now be described, by way of example, With reference to the accompanying drawings in which FIGS. 1 through 10 illustrate the present invention being an illuminated lens device for a welder's helmet.

Turning to FIG. 1, shown therein is a perspective illustration depicting a welder 12 wearing conventional arc welding safety equipment 14 for the face and eyes 18. Welders 12 are constrained by the equipment which is designed to provide them with a certain level of safety. The welder 12 must jerk the protective face shield 14 down while simultaneously trying to start the arc 20, keeping in mind the location of the work piece 16.

Figure 2:
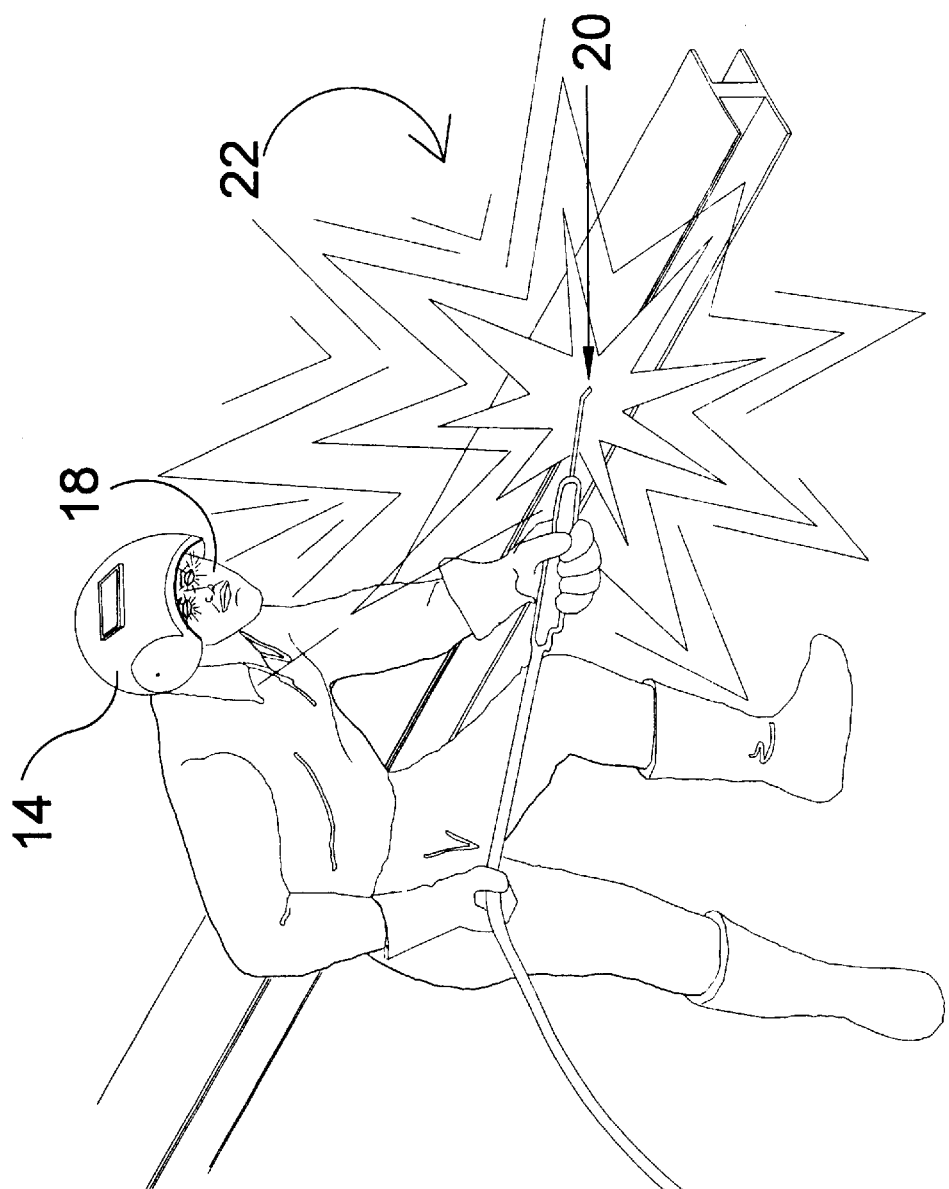
FIG. 2 is a perspective view of the possible danger of flash to the eyes of a welder. If the welders protective face shield is not down while starting the arc, dangerous flash may occur to the welder's eyes.
Figure 2:
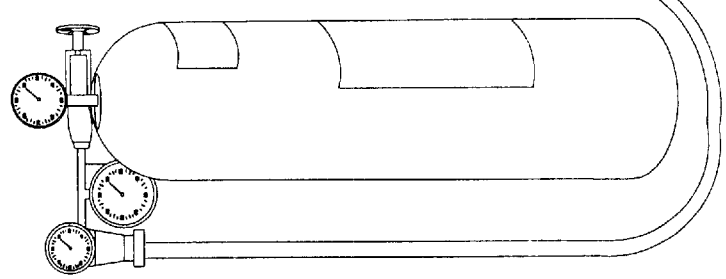

Turning to FIG. 2, shown therein is a perspective view of the possible danger of flash to the eyes 18 of a welder 12. If the welder's protective face shield 14 is not down while starting the arc 20, a dangerous flash 22 may occur to the welder's eyes 18.

Figure 3:
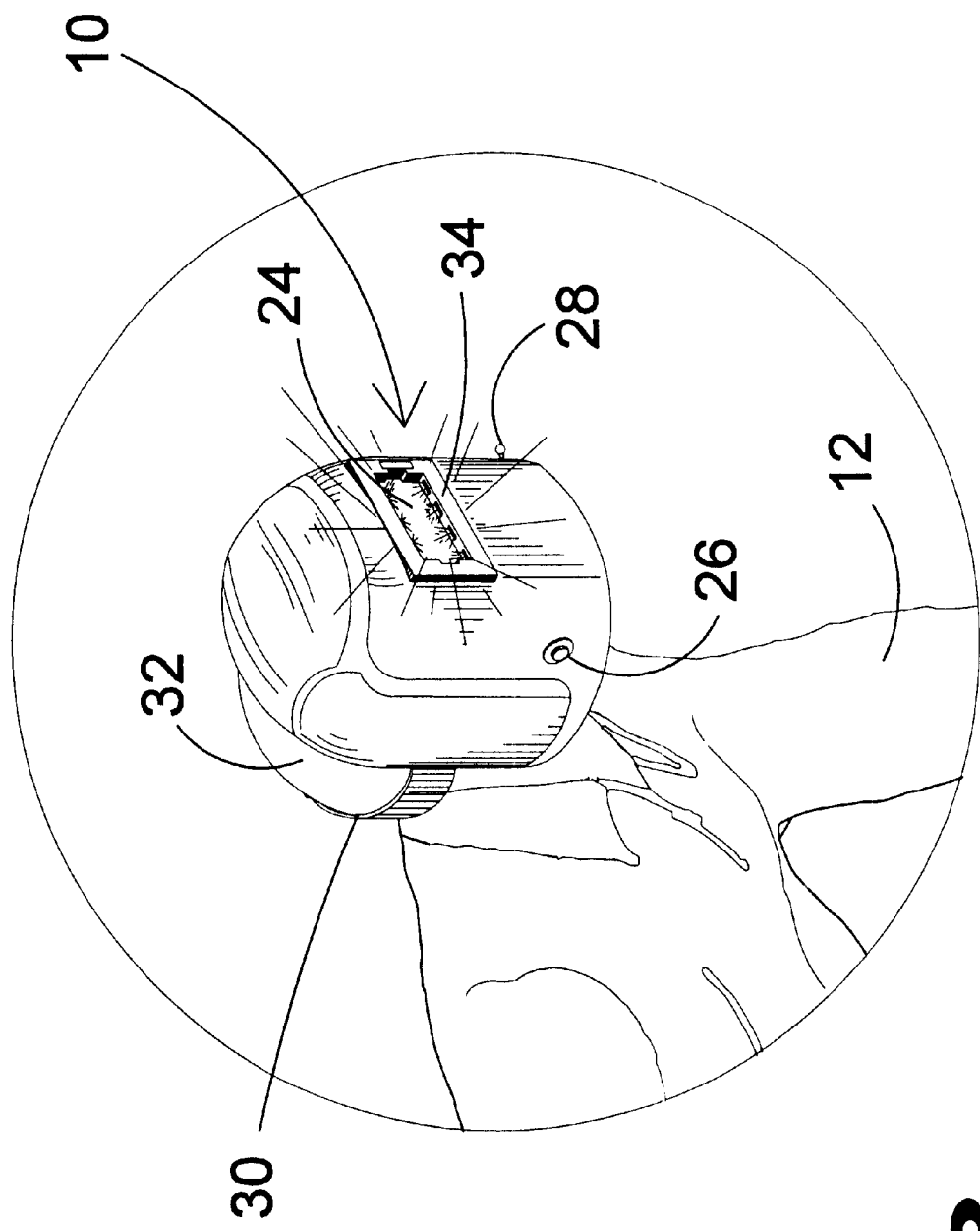
FIG. 3 is a partial view of a welder wearing an illuminated lens helmet of the present invention. The illuminated lens is controlled by a time delay button. The illuminated lens is powered prior to the ignition of the arc.

Turning to FIG. 3, shown therein is a partial view of a welder 12 wearing an illuminated lens helmet of the present invention 10. The illuminated lens 24 is illuminated by multiple lens lights 34 controlled by a time delay button 26. The illuminated lens light 34 is activated prior to the ignition of the arc. An on/off switch 28 is shown along with the head band 30 which holds the present invention 10 onto the head 32 of the user 12.

Figure 4:
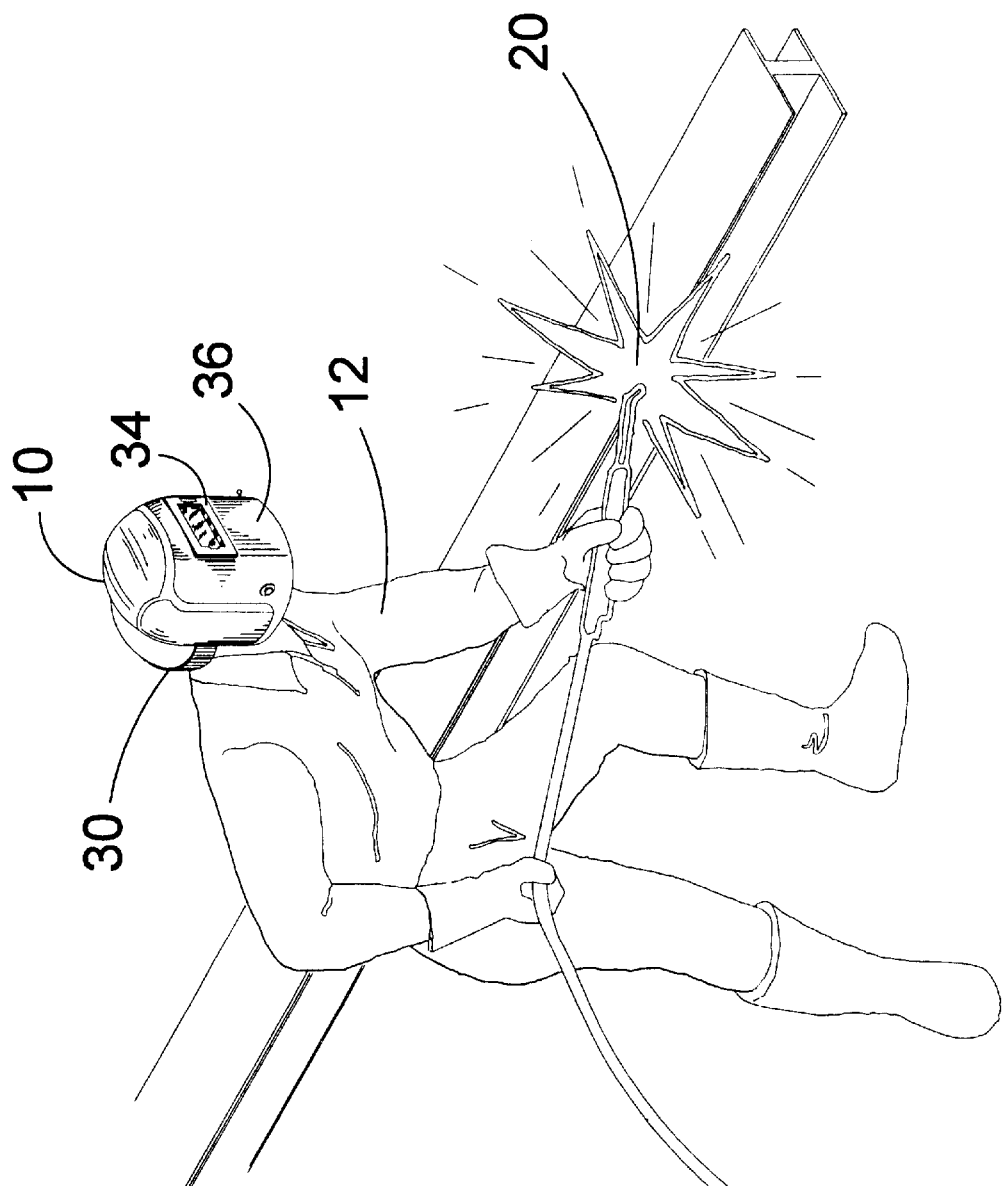
FIG. 4 is a perspective view of a welder wearing an illuminated lens helmet of the present invention. The welder's helmet is in the down position, the illuminated light is on and the arc is ignited.

Turning to FIG. 4, shown therein is a perspective view of a welder 12 wearing an illuminated lens helmet of the present invention 10. The welder's helmet 36 is in the down position, the illuminated light 34 is on and the arc 20 is ignited. Head band 30 is also shown.

Figure 5:
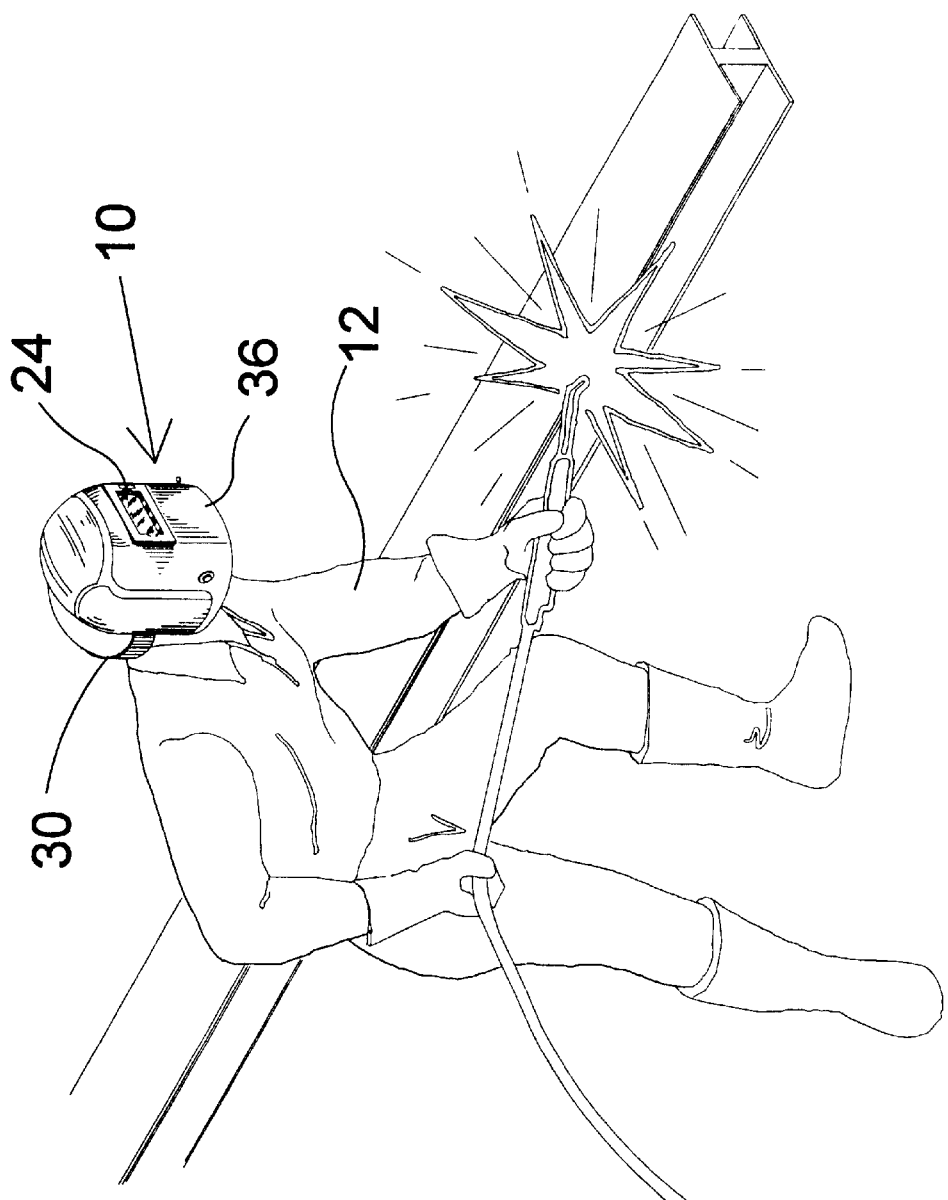
FIG. 5 is a perspective view of a welder wearing an illuminated lens helmet. The helmet does not need to be jerked down since it will be in place and the welder can see through the illuminated lens, prior to welding.
Figure 5:
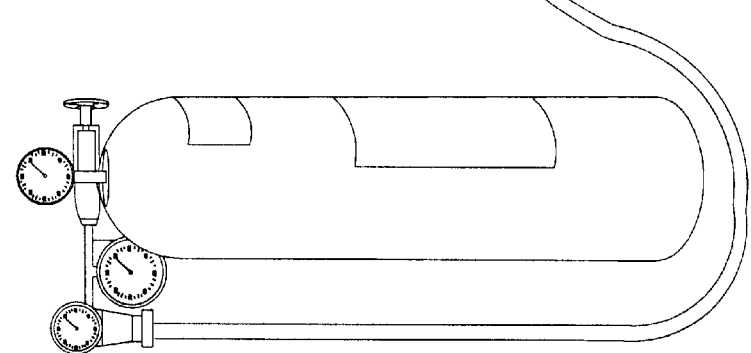

Turning to FIG. 5, shown therein is a perspective view of a welder 12 wearing an illuminated lens helmet 10. The helmet 36 does not need to be jerked down since it will be in place and the welder 12 can see through the illuminated lens 24, prior to welding. Head band 30 is also shown.

Figure 6:
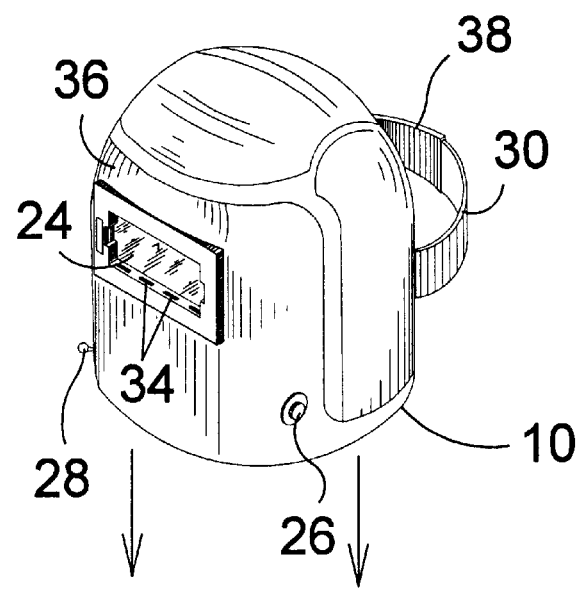
FIG. 6 is a perspective view of a welder being fitted with the illuminated lens helmet. The illuminated lens helmet is attached to the welder's face by means of an adjustable head band. When the illuminated lens helmet is worn by a welder, it provides light for the welder to see by until the arc is started. The light mounts to the shield around the viewing lens. Lens light is controlled by a button, as illustrated, on the face shield. The light has a timer which will allow the welder to turn the lens light on and get in place. After a pre-determine length of time, the welder should have started the arc and can see the work by that light.
Figure 6:
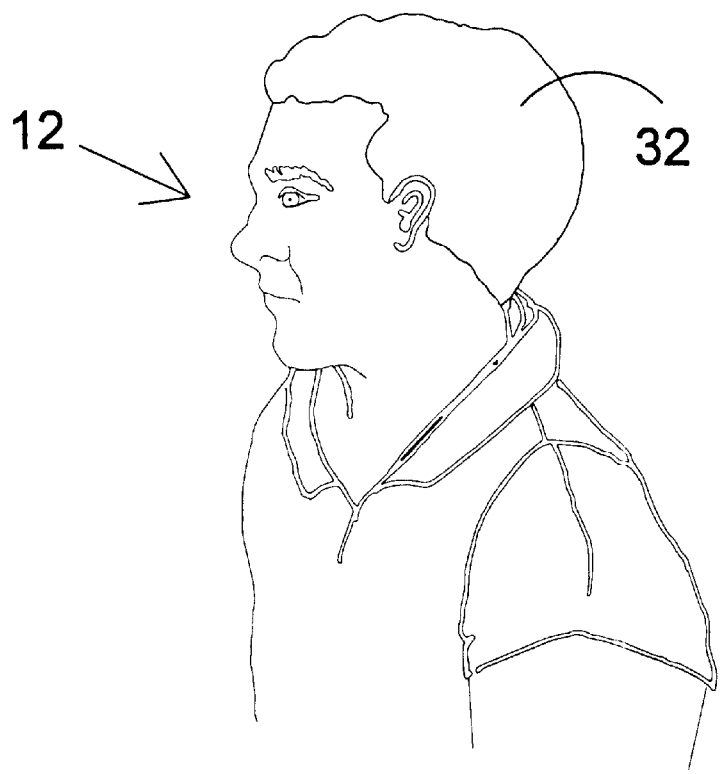

Turning to FIG. 6. shown therein is a perspective view of a welder 12 being fitted with the illuminated lens helmet 10. The illuminated lens helmet 10 is attached to the welder's head 32 by means of an adjustable head band 30 having size adjustment means 38. When the illuminated lens helmet is worn by a welder 12, it provides light for the welder to see by until the arc is started. The multiple lens lights 34 mounts to the face shield 36 around the viewing lens 24. Lens light 34 is controlled by an on/off button 28, as illustrated, on the face shield 36. The light has a timer 26 which will allow the welder 12 to turn the lens light on and get in place. After a pre-determine length of time, the welder 12 should have started the arc and can see the work by arc light.

Figure 7:
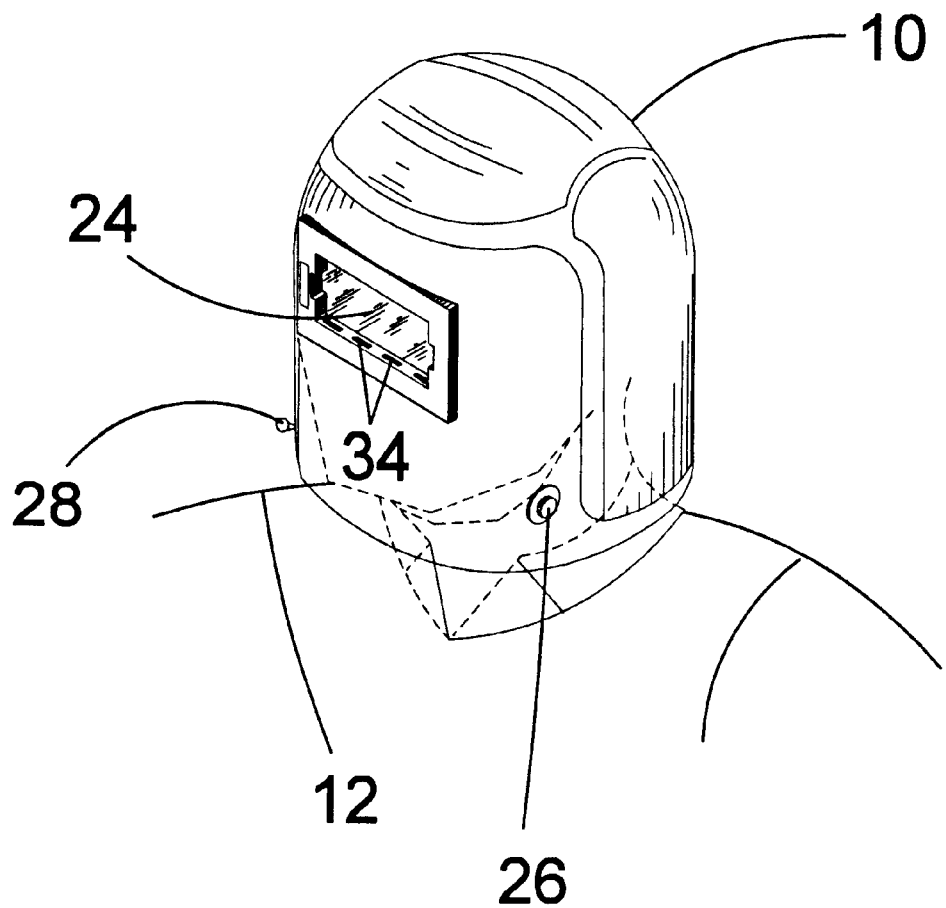
FIG. 7 is a perspective illustration depicting a welder wearing the illuminated lens helmet of the present invention. The illuminated lens helmet is attached to the welder's face by means of an adjustable head band. When the lens illuminated lens helmet is worn by a welder, it provides light for the welder to see by until the arc is started. The light mounts to the shield around the viewing lens. The light is controlled by a button, as illustrated, on the face shield. The light has a timer which will allow the welder to turn the lens light on and get in place. After a pre-determine length of time, the welder should have started the arc and can see the work by that light.

Turning to FIG. 7, shown therein is a perspective illustration depicting a welder 12 wearing the illuminated lens helmet of the present invention 10. The illuminated lens helmet 10 is attached to the welder's head by means of an adjustable head band. When the light illuminated lens helmet is worn by a welder 12, it provides light for the welder to see by until the arc is started. The lights 34 mount to the shield or lens 24 around the viewing lens. The light is controlled by an on/off button 28, as illustrated, on the face shield. The light 34 has a timer 26 which will allow the welder to turn the lens light 34 on and get in place. After a pre-determine length of time, the welder 12 should have started the arc and can see the work by the arc light.

Figure 8:
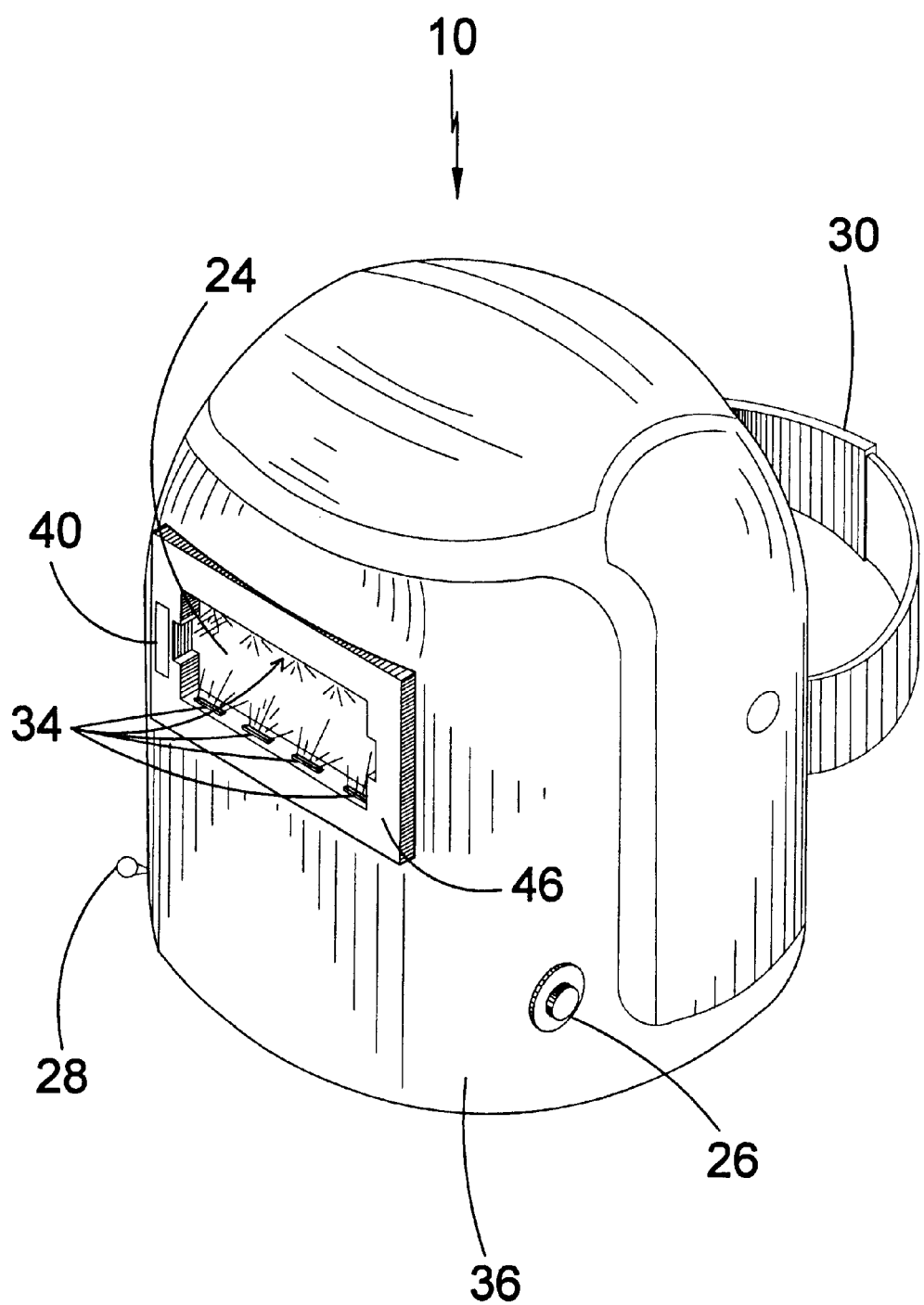
FIG. 8 is a perspective view of the illuminated lens helmet of the present invention. Depicted are the lights which illuminate the welding lens, the battery door, power switch, time delay button and adjustable head band.

Turing to FIG. 8, shown therein is a perspective view of the illuminated lens helmet of the present invention 10. Depicted are the lights 34 which illuminate the welding lens 24, the battery door 40, power switch 28, time delay button 26 and adjustable head band 30. The beams of lights 34 travel parallel to the plane of lens 24 to avoid glares and/or reflections. Also shown is rectangular frame 46 mounted into the wall of the helmet 36 at eye level having the lights 34 and battery door 40 mounted therein.

Figure 9:
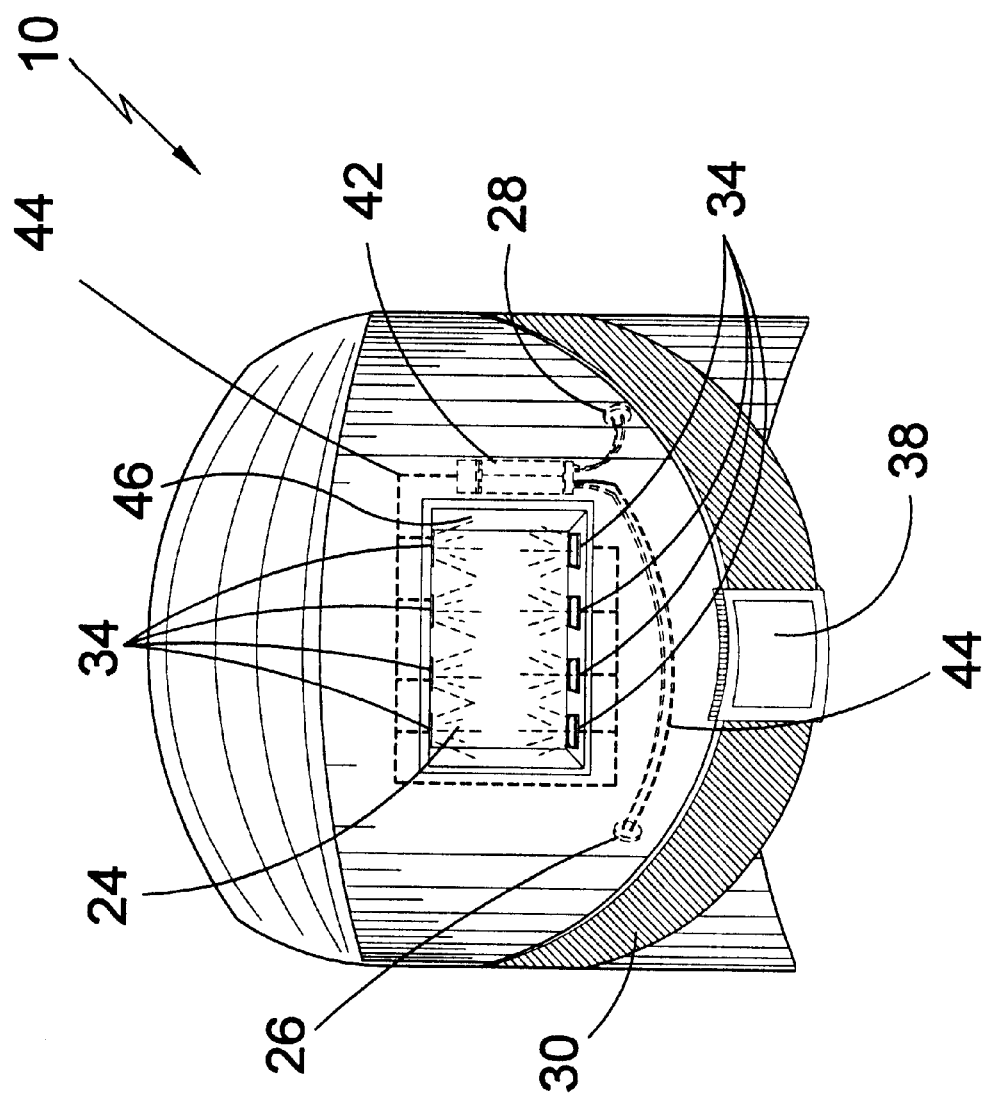
FIG. 9 is a rear view of the illuminated lens helmet of the present invention. Depicted are the lights which illuminate the welding lens, the battery door, the power switch, time delay button and adjustable head band.

Turning to FIG. 9, shown therein is a rear view of the illuminated lens helmet of the present invention 10. Depicted are the lights 34 which illuminate the welding lens 24, the battery compartment 42, the power switch 28. time delay button 26 and adjustable head band 30 for securing the helmet to the head of the welder. Size adjustment means 38 is also shown along with appropriate electrical connection means 44, e.g., wire, for electrically connecting all electrical components of the present invention. Frame 46 is also shown.

Figure 10:
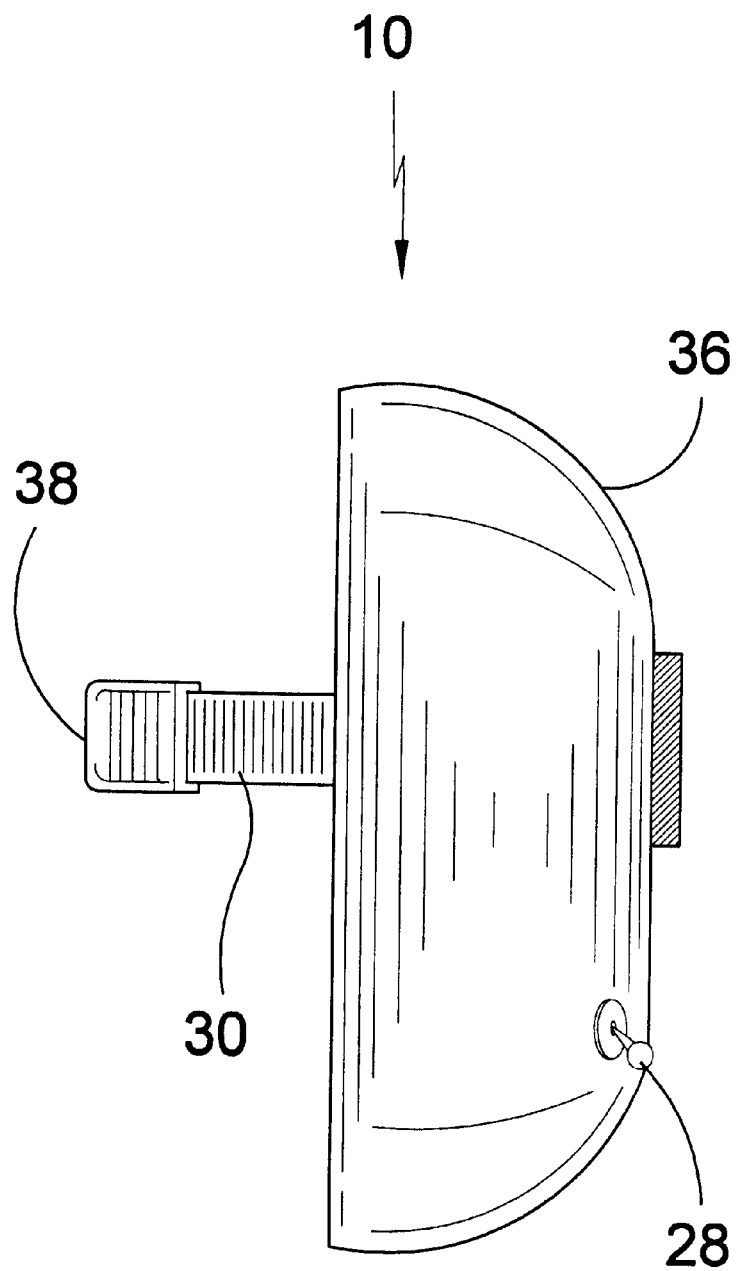
FIG. 10 is a side view of the illuminated lens helmet of the present invention. Depicting the shape of the illuminated lens helmet from a side perspective, the adjustable head band provides means for adjusting the helmet to the welder's head.

Turning to FIG. 10, shown therein is a side view of the illuminated lens helmet 36 of the present invention 10. Depicting the shape of the illuminated lens helmet 36 from a side perspective, the adjustable head band 30 provides means for adjusting 38 the helmet to the welder's head. The on/off switch 28 is also shown.

What is claimed to be new and desired to be protected by letters patent is set forth in the appended claims.

I claim:

1. An apparatus for illuminating a lens of a face shield to be worn by a welder, the improvement comprising:
   a) a plurality of lights disposed about the lens of the face shield;
   b) a plurality of light beams illuminating from said lights, said light beams travelling parallel to a plane of the lens of the face shield;
   c) a power supply for said lights disposed on the face shield;
   d) an on/off switch for said lights disposed on the face shield;
   e) a time delay switch for delaying the delivery of power to said lights; and
   f) electrical connecting means disposed on the face shield for electrically connecting said lights, said power supply, said time delay switch and said on/off switch.

2. The apparatus of claim 1, said power supply further comprising a battery.

3. The apparatus of claim 1, said power supply further comprising a plurality of batteries.

4. The apparatus of claim 1, said electrical connecting means further comprising electrical wire.

5. The apparatus of claim 1, having means comprising a head band for securement of the face shield about the head of the welder.

6. The apparatus of claim 5, said head band further comprising means for size adjustment.

7. An apparatus for illuminating a face shield to be worn by a welder, comprising:
  a) a frame disposed in a wall of the face shield, said frame being substantially rectangular shaped, said frame disposed at eye level of the welder;
  b) a transparent lens disposed in said frame whereby the welder can see through said lens;
  c) a plurality of lights disposed about the lens of the face shield;
  d) said lights mounted onto said frame;
  e) a plurality of light beams illuminating from said lights, said light beams travelling parallel to a plane of the lens of the face shield;
  f) a power supply for said lights disposed on the face shield;
  g) an on/off switch for said lights disposed on the face shield;
  h) a time delay switch for delaying the delivery of power to said lights; and
  i) electrical connecting means disposed on the face shield for electrically connecting said lights, said power supply, said time delay switch and said on/off switch.

8. The apparatus of claim 7, said power supply further comprising a battery.

9. The apparatus of claim 7, said power supply further comprising a plurality of batteries.

10. The apparatus of claim 7, said electrical connecting means further comprising electrical wire.

11. The apparatus of claim 7, having means comprising a head band for securement of the face shield about the head of the welder.

12. The apparatus of claim 11, said head band further comprising means for size adjustment.

* * * * *